US009439449B2

(12) United States Patent
Holvoet et al.

(10) Patent No.: US 9,439,449 B2
(45) Date of Patent: Sep. 13, 2016

(54) **NUTRITIONAL COMPOSITION COMPRISING *BIFIDOBACTERIUM LONGUM* STRAINS AND REDUCING FOOD ALLERGY SYMPTOMS, ESPECIALLY IN INFANTS AND CHILDREN**

(75) Inventors: Sebastien Holvoet, Savigney (CH); Annick Mercenier, Bussigny (CH); Adrian Zuercher, Bern (CH)

(73) Assignee: Nestec S.A., Vevey (CH)

( * ) Notice: Subject to any disclaimer, the term of this patent is extended or adjusted under 35 U.S.C. 154(b) by 345 days.

(21) Appl. No.: 13/391,172

(22) PCT Filed: Aug. 11, 2010

(86) PCT No.: PCT/EP2010/061666
§ 371 (c)(1),
(2), (4) Date: Feb. 17, 2012

(87) PCT Pub. No.: WO2011/020748
PCT Pub. Date: Feb. 24, 2011

(65) Prior Publication Data
US 2012/0164109 A1    Jun. 28, 2012

(30) Foreign Application Priority Data
Aug. 18, 2009  (EP) .................... 09168049

(51) Int. Cl.
| *A61K 35/00* | (2006.01) |
| *A23L 1/30* | (2006.01) |
| *A23L 1/29* | (2006.01) |
| *A23L 1/305* | (2006.01) |
| *A23L 1/308* | (2006.01) |
| *A61K 35/74* | (2015.01) |

(52) U.S. Cl.
CPC .............. *A23L 1/3014* (2013.01); *A23L 1/296* (2013.01); *A23L 1/3002* (2013.01); *A23L 1/3053* (2013.01); *A23L 1/3081* (2013.01); *A61K 35/74* (2013.01); *A23V 2002/00* (2013.01)

(58) Field of Classification Search
None
See application file for complete search history.

(56) References Cited

FOREIGN PATENT DOCUMENTS

| EP | 1227152 | 7/2002 |
| EP | 1854468 | 11/2007 |
| EP | 1858336 | 11/2007 |
| JP | 10309178 | 11/1998 |
| JP | 2006028050 | 2/2006 |
| JP | 2006273852 | 10/2006 |
| JP | 2009060800 | 3/2009 |
| WO | WO 9700078 | 1/1997 |
| WO | WO 2005039319 | 5/2005 |
| WO | WO 2006097415 | 9/2006 |
| WO | WO 2007093619 | 8/2007 |
| WO | WO 2008153377 | 12/2008 |
| WO | WO 2009072889 | 6/2009 |

OTHER PUBLICATIONS

Medina et al., Clinical and Experimental Immunology, 150: 531-538.*
Menard et al. Applied and Environmental Microbiology, Feb. 2008, p. 660-666 vol. 74, No. 3.*
Tokura et al., Bioscience, Biotechnology, and Biochemistry 69.10 (2005): 1974-1977.*
Frossard et al., Expert Opin. Biol. Ther. (2008) 8(9):1309-1317.*
Menard O et al: "Gnotobiotic mouse immune response induced by *Bifidobacterium* sp. strains isolated from infants," Applied and Environmental Microbiology, Feb. 2008 American Society for Microbiology US, vol. 74, No. 3, Feb. 2008, pp. 660-666; XP002573761.
Search Report for International Application No. PCT/EP2010/061666 mailed Oct. 4, 2010.
Akiyama et al., "Dietary unripe apple polyphenol inhibits the development of food allergies in murine models", FEBS Letter 579 (2005) 4485-4491.

* cited by examiner

*Primary Examiner* — Irene Marx
(74) *Attorney, Agent, or Firm* — K&L Gates LLP

(57) ABSTRACT

A complete nutritional composition comprising *Bifidobacterium* strains or probiotic is provided for reducing the symptoms of allergies originating from food allergens in young children or infants. Preferably the composition reduces symptoms of allergies (secondary prevention) and also reduces sensitization (primary prevention). The composition comprises a probiotic of the genus *Bifidobacterium*.

13 Claims, 7 Drawing Sheets

FIG. 1: Cytokine secretion by Th2-skewed human PBMC after co-culture with various strains of *B. longum*

| | Cytokine production (% of reference) | | | |
|---|---|---|---|---|
| | IFNγ[a] | IL-10[b] | IFNγ/IL1 | IL-5[c] |
| *B. longum* NCC 2705 | 60.4 | 47.6 | 1.3 | 45.9 |
| *B. longum* NCC 3001 (BB536) | 63.4 | 13.6 | 4.7 | 81.9 |
| *B. longum* NCC 435 (BL23) | 19.1 | 4.3 | 4.4 | 44.8 |

[a] Amount of IFNγ induced by stimulation with purified *E. coli* LPS = 100%

[b] Amount of IL-10 induced with a reference bacterial strain with proven ability to induce IL-10 = 100%

[c] Amount of IL-5 induced in absence of any stimulation (medium) = 100%.

FIG. 2: mRNA expression by Th2-skewed human PBMC after co-culture with *B. longum* NCC 2705 or *B. longum* NCC 3001 (BB536)

| | mRNA level (relative expression)[a] | | | | | | |
|---|---|---|---|---|---|---|---|
| | medium | | NCC 2705 | | NCC 3001 | | LPS |
| | 10 h | 24 h | 10 h | 24 h | 10 h | 24 h | 24 h |
| IFNγ | 103 | 119 | 5406 | 8529 | 5719 | 8363 | 11917 |
| IL-10 | 131 | 130 | 1789 | 532 | 906 | 228 | 101 |
| Tbet | 860 | 509 | 1584 | 1317 | 1740 | 1266 | 1617 |
| IL-5 | 8 | 18 | 24 | 23 | 26 | 24 | 7 |
| GATA-3 | 1575 | 1043 | 977 | 621 | 1099 | 673 | 803 |

[a] relative expression is based on levels of 3 housekeeping genes

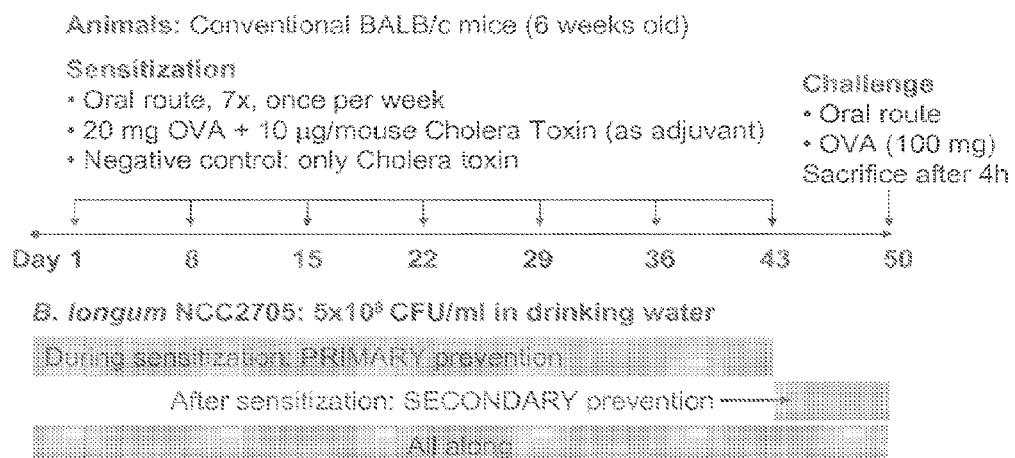
FIG. 3: Schematic description of OVA food allergy model

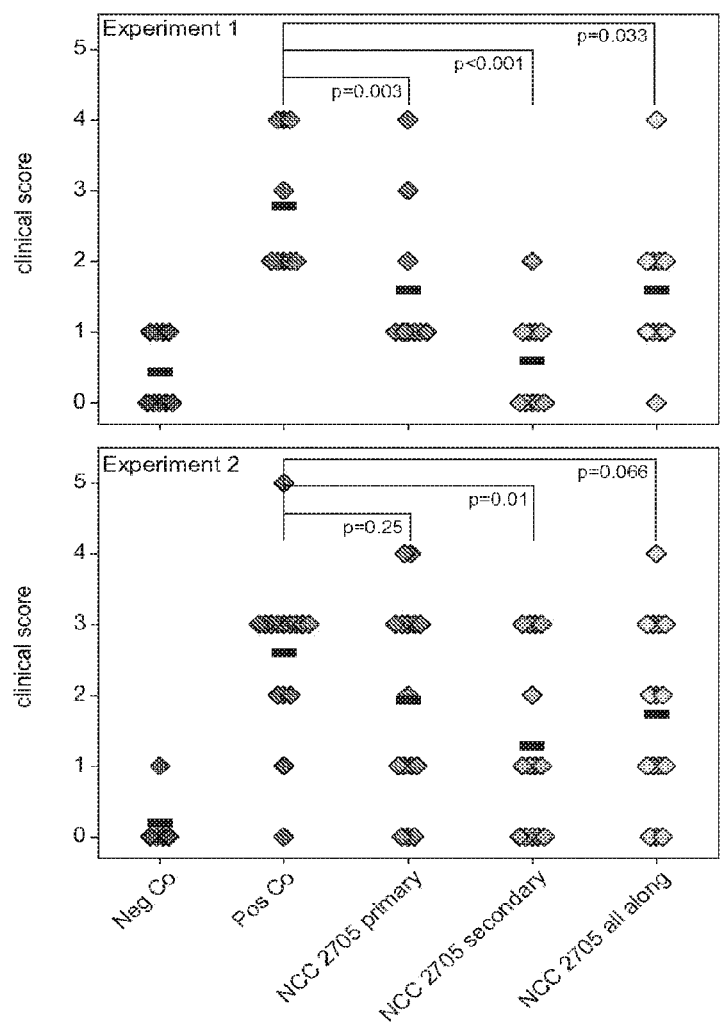
FIG. 4: Reduced symptoms of food allergy in mice receiving $5 \times 10^8$ CFU/ml of *B. longum* NCC 2705 in drinking water. Results of 2 independent experiments. Diamonds refer to individual mice, bar indicates mean.

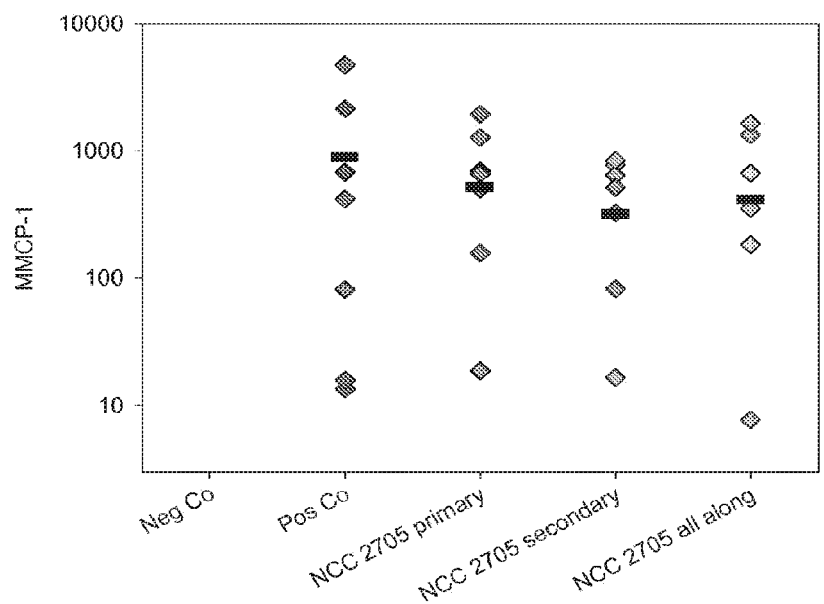
FIG. 5: Serum levels of Mouse Mast-Cell Protease 1 (MMCP-1) 4 hours after challenge. Diamonds refer to individual mice, bars indicate median.

FIG. 6: Cytokine production by mesenteric LN lymphocytes restimulated *ex vivo*

| | Cytokine (median pg/ml) | | | | | | | |
|---|---|---|---|---|---|---|---|---|
| | IL-1 | IL-2 | IL-4 | KC | TNFα | IFNγ | IL-5 | IL-10 |
| Neg. Co (n=5) | 17.3 | 1006.0 | 4.6 | 100.0 | 26.3 | 81.1 | 35.8 | 75.7 |
| Pos. Co (n=15) | 35.0 | 2824.1 | 260.2 | 259.8 | 81.7 | 502.6 | 270.4 | 479.8 |
| NCC 2705 primary (n=15) | 28.2 | 1862.7 | 185.2 | 231.8 | 67.9 | 257.5 | 237.6 | 327.1 |
| NCC 2705 secondary (n=14) | 36.9 | 1689.7 | 279.3 | 227.5 | 47.4 | 488.7 | 345.0 | 460.9 |
| NCC 2705 all along (n=15) | 42.6 | 2180.3 | 260.2 | 320.1 | 63.1 | 914.1 | 216.5 | 483.1 |

Results from 1 representative experiment are shown

FIG. 7: Gene expression levels in ileum

| | Neg Control | | Pos Control | | NCC 2705 primary[a] | | NCC 2705 secondary[b] | |
|---|---|---|---|---|---|---|---|---|
| | Relative[c] | Fold[d] | Relative | Fold | Relative | Fold | Relative | Fold |
| IL-4 | 2±25 | 1 | 7±109 | 4.2 | 4±121 | 2.6 | 3±55 | 1.9 |
| IL-5 | 2±26 | 1 | 68±196 | 35.7 | 9±67 | 4.7 | 24±60 | 12.6 |
| IL-9 | 2±9 | 1 | 108±653 | 56.5 | 9±323 | 4.7 | 97±368 | 50.4 |
| IL-13 | 2±0 | 1 | 299±221 | 184.6 | 97±142 | 59.8 | 98±154 | 60.4 |
| CCR3 | 303±1186 | 1 | 534±3155 | 1.8 | 1294±1341 | 4.3 | 2044±1843 | 6.7 |

[a] *B. longum* NCC 2705 was given for primary prevention to mice in drinking water during sensitization (day 1-43)
[b] *B. longum* NCC 2705 was given for secondary prevention to sensitized mice in drinking water for 1 week before challenge
[c] Relative gene expression levels were normalized to 3 house keeping genes (GAPDH, β-actin, HPRT)
[d] Fold expression was normalized to expression levels in the Neg Control group

NUTRITIONAL COMPOSITION COMPRISING *BIFIDOBACTERIUM LONGUM* STRAINS AND REDUCING FOOD ALLERGY SYMPTOMS, ESPECIALLY IN INFANTS AND CHILDREN

CROSS REFERENCE TO RELATED APPLICATIONS

The present application is a National Stage of International Application No. PCT/EP2010/061666, filed on Aug. 11, 2010, which claims priority to European Patent Application No. 09168049.6, filed on Aug. 18, 2009, the entire contents of which are being incorporated herein by reference.

FIELD OF THE INVENTION

This invention relates to the use of probiotics, especially *Bifidobacterium longum* strains in the manufacture of a nutritional composition for reducing the allergic symptoms of allergic patients when exposed to allergens.

BACKGROUND TO THE INVENTION

Allergies are among the most common health problems affecting the life of patients of all age. Allergic diseases are nowadays recognized as an epidemic by the World Health Organization (WHO). The prevalence of allergies has been shown to increase in the past decades. Modern life style, especially urban, has been associated with high prevalence and higher severity of allergic manifestations.

Allergic sensitization in childhood, especially in early childhood and especially to food allergens, is critical and of highest interest as development of an "allergic phenotype" or "atopy" has been shown to facilitate subsequent sensitization to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblöm et al 2008). Children with milder forms of food hypersensitivity also have increased risk for development of respiratory allergies but to a lesser degree than children with persistent food hypersensitivity. Therefore, attenuating the severity of food hypersensitivity may be crucial for slowing down the "Atopic March". In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Prevention of Allergies Can be Achieved on Different Levels:

"Primary prevention" is the effect of preventing or reducing the risk of sensitization of patients to allergens, characterized by absence or reduced levels of allergen-specific IgE antibodies. Preventing or reducing sensitization will result in absence or reduction of allergic symptoms upon exposure to the same allergen. By modulating the way a patient gets sensitized in regard to one allergen or one group of allergens (primary prevention), the subsequent allergic response may also be modulated.

"Secondary prevention" is the effect of modulating the symptoms of allergies, i.e. the occurrence or intensity of the allergic reaction in patient already sensitized to one or several allergens when the patient is re-exposed to said allergen(s). By modulating the occurrence or intensity of the allergic symptoms (secondary prevention), the inconvenience associated with allergies is minimized.

Given these distinct concepts of allergy prevention it may be hypothesized that by virtue of their inherent mechanisms of action, some compounds might act solely at one or at both of these specific levels of prevention. Some may, for example, solely reduce the sensitization to a specific allergen (primary prevention), while other compounds may solely have an effect on the secondary prevention and reduce the severity of allergic reactions. Other compounds may be able to influence both sensitization and symptoms and thus are effective in promoting primary and secondary prevention.

Food allergens are among the first allergens that infants encounter in their early life: typically, cow's milk proteins may be encountered by infants not receiving exclusive breast-feeding. Milk-proteins are indeed among the most frequently observed causes for food allergy in infancy, followed by eggs and wheat proteins. In general, food allergies can manifest by cutaneous (rash, eczema, others) and gastrointestinal symptoms (abdominal cramps; pain, especially in the abdomen; vomiting) in infants and young children. Further sensitization and episodes of allergies can also appear when the infant/young child is exposed to a novel food such as cereals, vegetables, fruits, nuts or fish.

Strains of *Bifidobacterium longum* (*B. longum*) have been describes to play an important role in the gut microbiota and to be associated with positive health effects: They are typically present at high numbers in the gut microbiota of healthy breast-fed infants. They can promote good digestion, boost the immune system, and produce lactic and acetic acid that controls intestinal pH. These bacteria can also inhibit the growth of *Candida albicans, E. coli*, and other bacteria with pathogenic characteristics. *B. longum* in general or specific strains of *B. longum* can be classified as probiotics according to the WHO definition.

To a certain extent specific strains of *B. longum* have been described to have an antiallergenic effect For example, patients suffering from allergic rhinitis due to Japanese cedar pollinosis showed reduced allergic symptoms after consumption of *B. longum* BB536 for several weeks before and during the pollen season (Xiao J Z, Kondo S, Yanagisawa N, Takahashi N, Odamaki T, Iwabuchi N, Miyaji K, Iwatsuki K, Togashi H, Enomoto K, Enomoto T. Probiotics in the treatment of Japanese cedar pollinosis: a double-blind placebo-controlled trial. Clin Exp Allergy. 2006 November; 36(11):1425-35. Xiao J Z, Kondo S, Yanagisawa N, Takahashi N, Odamaki T, Iwabuchi N, Iwatsuki K, Kokubo S, Togashi H, Enomoto K, Enomoto T. Effect of probiotic *Bifidobacterium longum* BB536 [corrected] in relieving clinical symptoms and modulating plasma cytokine levels of Japanese cedar pollinosis during the pollen season. A randomized double-blind, placebo-controlled trial. J Investig Allergol Clin Immunol. 2006; 16(2):86-93.)

Furthermore various probiotic cultures or mixes of probiotics have been described for their effect on the allergic immune system: for example EP1858336 (WO2006697949), describes a mix of probiotics that can decrease the risk of allergies due to wheat flour albumin and globulins. JP2006028050 describes the skin allergy suppressive properties of compositions comprising probiotic bacteria such as *Lactobacillus* and *Streptococcus*. WO2009072889, by Jan knoll et al, describes a *Bifidobacterium* that can be used in improving the lung function of subjects suffering from dust mite allergy.

JP10309178 suggests how a human-originated *Bifidobacterium* may help in curing food allergy or in inducing peroral immune tolerance.

However there remains a need for specifically reducing allergic reactions and symptoms in the population of young children and infants. This is especially important when considering the maturation of both the intestinal and immune systems undergoing in young children and when considering the multiplicity of novel allergens that the young children are exposed to, especially around weaning.

The question of food born allergic reactions in the young age is even further complicated by the specific nutritional needs of infants and young children. Caloric intake, caloric density, variety of desirable nutrient, protein content and protein quality are all among the factors important to bring the most appropriate nutrition to infants and young children. The presence of micronutrients such as vitamins and minerals are also of importance, more specifically when their concentration is limited by specific recommended ranges corresponding to the age of the target patients. As such, for the young children and infants, the matrices of food delivery are inherently complex but they are also of less variety: for example infants, although potentially allergic, usually require a specific protein balance in a matrix of milk-derived proteins. The presence of such multiple nutrients can potentiate the effect of the food allergens. In such complex matrices, low key food allergens unable to trigger allergic manifestation alone can then become more powerful at initiating an allergic reaction. Similarly compounds that may neutralize allergens or act on allergy prevention may see their effect diminished or annihilated in such complex nutritional matrices. Specifically it is not predictable whether compounds usually recognized to act on allergy prevention would still be active, and to which extend, in complex matrices such as nutritional composition for infants or young children.

There is a need to bring relief in the symptoms of food allergies in populations of infants and young children that have a history of allergic episodes and/or are allergic.

There is a need to provide a complete nutritional composition that not only brings a variety of nutrients but also reduces the severity of allergic reactions.

There is a need for providing a nutritional composition modulating the allergic reaction of young patients suffering from light to moderate forms of allergies, as these patients have special needs dictated by the incomplete maturity of their intestinal and immune systems.

There is also a need for modulating allergic reactions in young children that do not tolerate stringent pharmaceutical molecules, for example by nutritional interventions such as including modulators of the immune system into the regular nutritional regimen.

There is a need for providing a nutritional composition modulating the allergic reaction of young patients at the time, and around the time of weaning when the intestinal tract undergoes substantial modification and when new solid foods, potentially containing new allergenic proteins, are introduced and hence the patient is particularly susceptible to the sensitization to food allergens.

There is a need for alleviating the symptoms of allergies by providing an effective composition, possibly by reducing the exposure to intact allergens, even though the composition may not directly reduce the sensitization to allergens.

There is a need for a composition that has a positive effect on secondary prevention of allergy while not necessarily acting on the primary prevention to the same allergies.

There is finally a need for a composition, most particularly suited for young patients that by reduction of symptoms can help to diminish the "allergic phenotype" and thus can lower sensitization later in life to new allergens. There is a need for attenuating the atopic march.

SUMMARY OF THE INVENTION

In a first aspect, the present invention provides a complete nutritional composition for reducing the symptoms of allergies originating from food in patients having allergies triggered by food allergens, especially in young patients, babies and infants.

In a second aspect, the present invention provides a composition that significantly promotes secondary prevention of allergic reactions triggered by food allergens, optionally while not affecting the primary prevention against the same allergens.

In a third aspect, the present invention provides a composition that comprises probiotics, especially belonging to the *Bifidobacterium* genus.

In another aspect of the invention the composition of the invention is especially effective for infants/young children at the time of weaning.

The invention further extends to reduction of the sensitization to other allergens later in life.

BRIEF DESCRIPTION OF THE DRAWING

FIG. 1: Cytokine profile of Th2-skewed human PBMC after co-culture with *B. longum* NCC 2705 deposited by Nestec SA under CNCM-I2618 or other strains.

FIG. 2: mRNA profile of Th2-skewed human PBMC after co-culture with *B. longum* NCC 2705 or other strains)

FIG. 3: Schematic description of OVA food allergy mouse model

FIG. 4: Illustration of the clinical score showing reduced symptoms of food allergy in mice receiving $5 \times 10^8$ CFU/ml of *B. longum* NCC 2705 in drinking water.

FIG. 5: Serum levels of Mouse Mast-Cell Protease 1 (MMCP-1).

FIG. 6: Cytokine production by mesenteric LN lymphocytes and splenocytes restimulated ex vivo.

FIG. 7: Gene expression levels in ileum.

DETAILED DESCRIPTION OF THE INVENTION

Definitions: In this specification, the following terms have the following meanings:

"Complete nutritional composition". For the purpose of this document a complete nutritional composition is a composition that comprises a significant amount, usually 20% or more, of the major nutritional nutrients recommended for a given age. Such major nutrients are usually provided in quantity and proportion such as to fulfill 20% or more of the specific recommended nutrient's doses for a given age, when used in adequate quantity for providing the recommended caloric intake for a given age. A complete nutritional composition usually comprises a source of protein, a source of lipid, a source of carbohydrates in a balanced proportion that meets the general recommendation for a given age. It usually also include micronutrients such as vitamins and minerals, as well as a source of essential amino acids and a source of essential fatty acids. It is however understood that a complete nutritional composition may neither comprise all specific nutrients, nor all recommended amounts, to fulfill all nutritional needs of an infant or young child. A complete nutritional composition excludes compositions comprising merely *Bifidobacterium* or *Bifidobacterium* in a predominant proportion.

"Symptoms of allergies" generally include symptoms triggered by allergens. Such symptoms include cutaneous (redness of skin, rash, itchiness, dermatitis, eczema), ocular (itching and watering of the eyes), gastrointestinal (congestion, abdominal pain, cramps, vomiting diarrhea), respiratory (itching of the nose, nasal congestion, rhinitis, asthma) and in severe cases systemic (dizziness, mental confusion, anaphylaxis) manifestations.

"Primary prevention of allergies" means all measures aiming at avoidance or reduction of allergic (immunological) sensitization for example prevention or reduction of specific IgE antibodies.

"Secondary prevention of allergies" means prevention or reduction of the development of allergic disease/allergic symptoms in a sensitized individual.

"Weaning period" is the period during which infants are adapting from pure liquid nutrition to solid or semi-solid food, and adapting from quasi unique food type (generally mother milk or infant formula) to a variety of foods.

"Sensitization" means induction/development of allergen-specific IgE antibodies.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999: 10 107-10). The definition of probiotic is generally admitted and in line with the WHO definition. The probiotic can comprise a unique strain of micro-organism, of a mix of various strains and/or a mix of various bacterial species and genera. In case of mixtures the singular term "probiotic" can still be used to designate the probiotic mixture or preparation. For the purpose of the present invention, micro-organisms of the genus *Bifidobacterium* are considered as probiotics.

"Prebiotic" generally means a non digestible food ingredient that beneficially affects the host by selectively stimulating the growth and/or activity of micro-organisms present in the gut of the host, and thus attempt to improve host health.

*Bifidobacterium longum* (*B longum*) strain NCC 2705 (Nestle Collection reference 2705) is the *B. longum* strain having the international identification reference CNCM-I2618 (deposited on Jan. 29, 2001 at Collection Nationale de Cultures de Microorganismes at Institute Pasteur, 28 rue du Docteur Roux, F-75024, Paris, France).

The inventors have evidenced that allergic reaction and symptoms can be alleviated when sensitized young mammals are provided with a complete nutritional composition that comprises *B. longum* NCC 2705. This defined a positive effect on the secondary prevention of allergies.

This effect was accompanied by a slight but significant reduction of the sensitization of the young mammals to allergens (i.e. primary prevention of allergies was evidenced).

Effect of the Composition:

The invention relates to the use of micro-organisms of genus *Bifidobacterium*, more particularly *Bifidobacterium longum* (*B. longum*), and more specifically strain *B. longum* NCC 2705 for the manufacture of a complete nutritional composition for reducing the symptoms in patients having allergies triggered by food allergens. The inventors have evidenced that consumption of *Bifidobacterium longum* in general and *B. longum* NCC 2705 in particular leads to reduced symptoms of food allergy in a group of mice receiving a nutritional composition containing said strain of *Bifidobacterium*. This is evidenced when an allergic reaction (challenge) is induced after sensitization. The model mimics food allergy in humans, when humans (typically infants/young children) are naturally sensitized to food allergens and further re-exposed to said allergens. The bacterial strain *B. longum* NCC 2705 hence shows a protective effect.

In one embodiment of the invention the effect of the composition is more specifically an effect on the secondary prevention of allergies. The symptoms of allergies, in the mouse model, are indeed reduced significantly, as illustrated by a lower allergic clinical score. Generally the symptoms can include all or a selection of the usually recognized symptoms of allergies.

In one embodiment of the invention the symptoms comprise diarrhea, skin irritation or respiratory symptoms or combinations thereof.

In one embodiment of the invention the symptoms can be accompanied by release of biochemical mediators, such a tryptase, chymase, histamine, leukotriens.

In one embodiment of the invention the composition also has an effect on the sensitization of the patients to the allergens. Indeed a slight but significant primary prevention of allergies seems to be achieved by the composition comprising *B. longum* NCC 2705. The animals exhibited a lower sensitization to food allergens. The effect of the composition is in that regard of high interest as it both reduces the symptoms and reduces the sensitization, i.e. the risk of later symptoms upon re-exposure to allergens.

In one embodiment the composition reduces the sensitization to other allergens later in life. It is believed that the composition promotes (or at least does not block) the natural processes of immune maturation and hence, is able to have a long term effect on lowering the sensitization to the same allergens or to different allergens (reduction of sensitization later in life). By reducing the symptoms of allergy (secondary prevention) and the short term sensitization (as part of the primary prevention), it is hypothesized that the composition of the invention can still allow for the natural immune maturation to occur, and have such long term beneficial effect.

Composition of the Invention or for Use in the Invention:

The composition of the invention can be a complete nutritional composition such as an infant formula or can bring a substantial portion of the complete diet. Preferably the composition is a complete nutritional composition that brings all or almost all the nutritional requirements of the target body when taken as the sole source of nutrient. In one embodiment the composition comprises infant cereals. In another embodiment, such as a baby food, the composition brings a portion of the complete diet, preferably 50% or more or 20% or more (quantitatively and qualitatively). In one embodiment the composition comprises infant cereals. In one embodiment the composition may be a liquid composition for children comprising cereals or a baby food The probiotic used is of the *Bifidobacterium* genus. Although the inventors can not exclude that other probiotics would have a similar or related effect, no experimental data could prove that other genera or strains of probiotics are equally effective, besides the one observed for *Lactococcus lactis* NCC 2287 (SL131) CNCM I-4154 and *Lactococcus*

*lactis* NCC 2180 (SL60) CNCM I-4199 described in the co-pending application by the same inventors. In one embodiment of the invention the probiotic is strain *B. longum* NCC 2705 CNCM-I2618.

In one embodiment of the invention the composition comprise between $10^4$ and $10^{11}$ colony forming units (CFU) per g of the dry composition. When the composition is an infant formula the amount of probiotic in the infant formula can be between $10^5$ and $10^8$ CFU/g of infant formula. In one embodiment the composition comprises between $10^6$ and $5 \times 10^7$ CFU/g, that is in a dose demonstrated to have a physiological effect. In one embodiment it has been identified that probiotics at a low dose can have a beneficial effect, in particular when the composition also comprises prebiotics and proteins in a defined limited amount. In such embodiment the probiotics are present in the composition in an amount between $10^3$ and $10^5$ CFU/g. The prebiotics can by oligosaccharides and/or the proteins can be present in an amount not exceeding 4 g/100 kcal or less than 2 g/100 kcal or less than 1.8. g/100 kcal or less than 1.5 g/100 kcal of the composition.

The probiotic can be mixed together with the dry or wet composition of the invention. Treatments or specific processes can be applied to improve the stability or viability of the probiotics in the composition. The probiotic can be applied in a dry form or in a wet from. After mixing the probiotic with the composition the mix can be processed in a way that does not dramatically affect the viability of the probiotics. In another embodiment the probiotics are partly or fully inactivated before, during or after the mixing. In one embodiment the probiotics have been rendered inactivated and/or incapable to replicate prior to the use in the composition of the invention. This for example can be achieved by heat treatment or other described treatments.

In one embodiment of the invention, the composition comprises prebiotics. It is known that prebiotics comprise carbohydrates and more specifically, oligosaccharides. Furthermore it is known that they have widely been used as functional food ingredients. They resist hydrolysis by enzymes of the human digestive tract, can reach the colon undegraded and provide a carbohydrate substance particularly suited to the growth of bifidobacteria or other probiotics. Oligosaccharides may for example be produced from glucose, galactose, xylose, maltose, sucrose, lactose, starch, xylan, hemicellulose, inulin, or a mixture thereof. Purified commercially available prebiotic products such as fructooligosaccharides contain greater than about 95% solids in the form of oligosaccharides.

Preferably, an embodiment of the composition is a nutritional composition which comprises at least one prebiotic.

Preferably, an embodiment of the prebiotic comprises an oligosaccharide produced from glucose, galactose, xylose, maltose, sucrose, lactose, starch, xylan, hemicellulose, inulin, or a mixture thereof. More preferably the oligosaccharide comprises fructooligosaccharide. Most preferably the prebiotic comprises a mixture of fructooligosaccharide and inulin. Preferably this mixture comprises PREBIO1® or a mixture of commercially available RAFTILOSE® and RAFTILINE®.

Preferably, an embodiment of the prebiotic component of the composition comprises about 50% to about 90% fructooligosaccharide. More preferably it comprises about 60% to about 80% fructooligosaccharide. Most preferably it comprises about 70% fructooligosaccharide. Preferably, an embodiment of the prebiotic comprises about 10% to about 50% inulin. More preferably it comprises about 20% to about 40% inulin. Most preferably it comprises about 30% inulin. In one embodiment the prebiotic component may represent about between 0.1% and 10% of the composition.

In one embodiment, the composition of invention further comprises an apple extract comprising polyphenols. The apple extract can help reducing the symptoms of allergies originating from food in patients having allergies triggered by food allergens. As such the apple extract acts in a synergistic way with the probiotic *Bifidobacterium* in order to modulate, reduce, or attenuate allergies in patients having food allergies. In one embodiment such composition is used for baby food and/or baby cereals that naturally represent a suitable carrier for the composition. In a further embodiment the baby food or baby cereals comprises apple extracts or material from apple. In one embodiment of the invention the apple extract is the protein extract commercialized by Val de Vire Bioactives (Conde sur Vire, France) under the reference "Pomactiv HFV". In one embodiment the apple extract is similar to or derived from the cited Pomactiv HFV and has similar effect.

Hypothetical Mechanism of Action:

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, without being bound by the theory, it is hypothesized that allergy can be mitigated, down-regulated or prevented by restoring an appropriate balance between the Th1 and Th2 arms of the immune system. This implies the necessity to reduce the Th2 responses or to enhance, at least transiently, the Th1 responses. The former could be characterized by reduced production of Th2 cytokines such as IL-5, the latter could be characterized by increased production of Th1 cytokines such as IFNγ. Alternatively, in a sensitized individual, a general anti-inflammatory effect may be most desirable, e.g. through the induction of T-regulatory (Treg) cells, capable of down-modulating the effects of both Th1 and Th2 cells. This could be indicated by the ability of inducing secretion of IL-10.

In one embodiment of the invention the composition comprises hydrolyzed or partially hydrolyzed proteins. A nutritional composition based on (partially) hydrolyzed proteins is particularly suited to the immune system and gastrointestinal tract of infants/young children because hydrolyzed proteins are more easily digested and have reduced allergenicity compared to intact proteins. Furthermore, without being bound by the theory it can be hypothesized that hydrolyzed proteins might be a preferable substrate for probiotics or intestinal bacteria (especially those displaying a variety of peptidase activities) compared to intact proteins, leading to an improved effect of the probiotic strain and thus synergism between hydrolyzed proteins and probiotics. This represents a most appropriate composition for the immune system and gastrointestinal tract of a food-allergic infant/young child. In such instance the combination of *B. longum* NCC 2705 with hydrolyzed proteins is of highest relevance to the invention.

In one embodiment the hydrolyzed proteins are proteins hydrolyzed from whey and/or casein. In one embodiment the hydrolyzed proteins results from the action of trypsin and/or chymotrypsin on the proteins (esp. whey proteins). In one embodiment the hydrolyzed proteins comprise soy proteins or/and egg proteins. In one embodiment the hydrolyzed proteins result from the action of proteases such as Protamex® and/or Flavourzyme® (Novozyme, Denmark). In one embodiment the proteins of the composition, preferably the hydrolyzed proteins, comprise cereal or eggs proteins. In one embodiment the hydrolyzed proteins results from the action of Alcalase. The composition of the invention can comprise a mix of 2 or more of the cited protein sources.

Target Group:

The composition of the invention is most suitably targeted at relatively young patients, although an effect on adults is not excluded or is possible. Preferentially indeed the patients are sufficiently young to still going through a maturation phase of their immune system and their gastro-intestinal tract. In such patients the effect of the composition can be more intense or more rapid. In one embodiment the composition is an infant formula, infant cereal and/or a baby food. Preferably the composition is targeted at young humans below the age of 6 years, between birth and the age of 3 years or between birth and weaning. In one embodiment the composition is a starter or a follow-up infant formula. Preferably the nutritional composition comprises a vast majority of the necessary nutrients for the feeding of the young humans.

In one embodiment the nutritional composition is an infant cereal composition for infants/young children 1 to 4 years old. The composition can be more specifically targeted to and administered during the weaning period and/or up to 12 months thereafter. The weaning period is indeed important in regard to the invention as the infants are exposed to a variety of foods during the weaning period, while still undergoing maturation and re-organisation of their immune system and their gastro-intestinal tract. Effective control of the allergic response is therefore of particular importance during that period.

In regard to the use of the composition of the invention the children, babies or infants can be allergic children. Allergic children are those children, babies or infants having experienced at least one episode of allergic reaction—light, moderate or severe—to a food allergen. In one embodiment of the invention the children, babies or infants have declared severe allergies to food allergens and/or have experienced more than one moderate or severe episode of food allergy. The symptoms of allergies can include various known symptoms such as cutaneous irritation or redness, gastro-intestinal symptoms or respiratory symptoms.

The food allergens encompassed by the present invention can include all types of allergens naturally occurring or usually occurring in food, especially food for young humans (e.g. infants, babies, children).

Experimental Results:

Probiotics, predominantly belonging to the genera *Lactobacillus* and *Bifidobacterium* have been tested in human and animal trials for their ability to interfere with allergic sensitization or with development of allergic symptoms in sensitized individuals. Here we analyze whether a particular strain of *B. longum*, namely *B. longum* NCC 2705, has potential to mitigate development of allergic sensitization or symptoms.

In an initial step we developed and used an in vitro system based on human blood lymphocytes to determine cytokine profiles induced by different strains of *B. longum*. We assumed that the observed profiles would be predictive for cytokine production induced in vivo by the same strains and thus for the biological effects conferred by said strains.

Cells of an allergic individual or of an individual prone to allergy development are characterized by their propensity to produce Th2 cytokines. To partly mimic this status in vitro, we developed a cell culture model of Th2-skewed human peripheral blood mononuclear cells (PBMC) as an alternative to using PBMC of allergic donors. Th2-skewing was induced by culturing PBMC with interleukin (IL)-4+anti-CD40 antibody (as detailed in Methods); after 3 days of culture to induce Th2-skewing, bifidobacteria were added for an additional 48 hours, resulting in a total culture duration of 5 days. As a basic read-out the cytokines IFNγ, IL-10 and IL-5 were measured by ELISA in the supernatant of cells stimulated with *B. longum*.

FIG. 1 shows that *B. longum* NCC 2705 induced similar amounts of IFNγ and IL-10, leading to an IFNγ/IL-10 ratio of 1.3. Other *B. longum* strains analyzed in parallel such as *B. longum* NCC 3001 (BB536; deposited by Morinaga under ATCC BAA-999 and *B. longum* NCC 435 (BL23, ATCC 15707) had IFNγ/IL-10 ratios more skewed towards IFNγ. In addition, *B. longum* NCC 2705 was an efficient inhibitor of IL-5 secretion. These data suggest that *B. longum* NCC 2705 is a robust producer of IL-10 under Th2-skewed conditions and therefore might have an anti-allergic effect through anti-inflammatory activity.

FIG. 2 shows confirmation of these results on the mRNA level for *B. longum* NCC 2705 compared to *B. longum* BB536 and LPS (from *E. coli*). Expression levels of various genes were analyzed 10 and 24 hours after starting co-cultures of Th2-skewed human PBMC with the different stimuli. Culture of Th2-skewed PBMC with either *B. longum* NCC 2705 or NCC 3001 (BB536) led to moderate induction of IFNγ compared to LPS, a known strong inducer of IFNγ. IL-10 mRNA levels induced by *B longum* NCC 2705 were higher than induced by *B. longum* BB536. Levels of IL-5 mRNA were not affected whereas GATA-3 was slightly reduced after incubation with either of the strains. Altogether, these findings confirm the results obtained on the protein level (FIG. 1).

The in vivo effect of *B. longum* NCC 2705 was tested in a mouse food allergy model (OVA Food Allergy Mouse Model, illustrated in FIG. 3).

BALB/c mice were sensitized at weekly intervals with ovalbumin (OVA)+cholera toxin by the oral route during 7 weeks. In this model, oral challenge with a large dose of OVA at the end of the sensitization period leads to clinical symptoms such as diarrhoea, scratching episodes, bristled fur, cyanosis and loss of mobility. NCC 2705 was given to mice via drinking water ($5 \times 10^8$ CFU/ml; ad libitum) either during the sensitization phase from day 1 to 43 (primary prevention), during the last week of the experiments (day 43-50; secondary prevention) or all along the trial (day 1-50, all along).

FIG. 4 shows the clinical symptoms observed in two individual experiments. Mice treated with *B. longum* NCC 2705 developed significantly less severe clinical symptoms after challenge than sensitized, untreated animals (Positive Control). The effect was most pronounced in secondary prevention but still significant in primary prevention and when *B. longum* NCC 2705 was given all along (experiment 1, upper panel). In a second experiment, the protective effect in secondary prevention was corroborated, whereas trends for the effect in primary prevention or all along were observed (experiment 2, lower panel).

As shown in FIG. 5, in addition to the clinical score, mouse mast-cell protease 1 (MMCP-1) serum levels were determined as a measure of intestinal mast-cell activation by allergen challenge. OVA challenge led to a strong increase of serum levels of MMCP-1 in the Positive compared to the Negative Control group. A trend in the modulation of MMCP-1 serum levels (although not significant) was observed in mice treated with NCC 2705 compared to the Positive Control group.

FIG. 6 shows cytokine production by ex vivo restimulated lymphocytes. For this purpose, lymphocytes from mesenteric lymph nodes (MLN) were collected after challenge, restimulated with 1 mg/ml of OVA and cultured for 72 hours. Levels of IL-1, IL-2, IL-4, KC, TNFα, IFN-γ, IL-5 and IL-10 were measured by multiplex assay (Mesoscale®). MLN lymphocytes of mice treated with NCC 2705 in primary prevention produced less IL-2, IL-4, TNFα, IFNγ, IL-5 and IL-10 compared to the Positive Control.

Expression levels in the intestine of various genes associated with allergy were determined by quantitative real-time polymerase chain-reaction (qRT-PCR—see method below). The measurements of gene expression were performed on tissues from ileum for the positive control group, the negative control group and the group receiving *B. longum* NCC 2705 during the sensitization period (primary prevention) and during the last week before challenge (secondary prevention). FIG. 7 illustrates the results obtained: sensitization led to up-regulation of mRNA transcription for typical Th2 cytokines such as IL-4, IL-5, IL-9 and IL-13 (Neg Co vs. Pos Co) as well s IL-10. Treatment with NCC 2705 (primary or secondary prevention) led to marked down-regulation of these markers.

Hence the experiments demonstrate the down-modulation of immune responses by reduction of expression of relevant genes when animals received *B. longum* NCC 2705 (primary and secondary prevention). This is believed to be contributing to the anti-allergic effect of the tested strain of *Bifidobacterium* in the reduction of food allergy in this model.

Conclusion: These data show that consumption of *B. longum* NCC 2705 by a sensitized animal leads to reduced allergic symptoms upon exposure to the sensitizing allergen. Similarly but less marked, consumption of *B. longum* NCC 2705 during the sensitization phase had a protective effect (primary prevention). This finding was paralleled by reduced secretion of cytokines by mesenteric lymph node cells as well as diminished expression of key genes related to allergy in the intestine, suggesting that a modulation of components of the immune system, contributed to the protective effect.

Analytical Methods:

Reagents and Bacterial Biomass:

Bacterial biomass was produced by culture of each strain under optimal conditions in liquid cultures. Growth kinetics were determined for each strain and according to these, biomass was harvested 3 h after reaching the stationary phase. At this time-point cultures were washed 2× in cold PBS and frozen in PBS 20% glycerol at −80° C. in 50 µl aliquots. LPS (from *E. coli*) was purchased from Sigma (Buchs, Switzerland).

Isolation and Culture of Th2-Skewed Human PBMC:

Human peripheral blood mononuclear cells (PBMC) were isolated from filters obtained from the "Centre de Transfusion of the CHUV". The cells trapped in the filters were flushed back into the blood collection bag with 90 ml of Hanks balanced salt solution (HBSS) (Sigma). The cells were diluted 1:2 with HBSS and the PBMC were isolated by density gradient centrifugation on Histopaque 1077 (Sigma). The cells at the interphase were collected and washed two times with HBSS. The PBMC were resuspended in Iscove's Modified Dulbecco's Medium (cIMDM) (Sigma) complemented with 10% fetal bovine serum FBS (Bioconcept, Paris, France) 1% L-glutamine (Sigma) 1% Penicillin/Streptomycin (Sigma) and 0.1% Gentamycin (Sigma). The cells were cultured in 48 wells plate (Milian, Meyrin, Switzerland) at $1.5 \times 10^6$ cells/ml in the presence of 50 ng/ml of IL-4 (Bioconcept) and 1 µg/ml of anti-CD40 antibody (R&D Systems, Abington, England) in cIMDM to induce a Th2 cytokine phenotype. LPS was used at 1 µg/ml. After 3 days of culture, probiotics were added at $10^7$, $10^6$, and $10^5$ CFU/ml. After adding ingredients, PBMC culture was continued for an additional 48 h resulting in total culture duration of 5 days.

Cytokine ELISA:

Human IFN-γ, human IL-5, human IL-10, mouse IFN-γ, mouse IL-13, and mouse IL-10 cytokines were measured using DuoSet kits from R&D systems according to the manufacturer's instructions.

Evaluation of ELISA Results:

OD values were transformed into pg/ml using the standard curves. To adjust for the large donor-to-donor variation generally observed with PBMC from different human donors, data were standardized according to an arbitrary internal standard. The pg/ml value of IFN-γ obtained for each donor by stimulation with LPS was set to 100%. For normalization of IL-10 values, the amount of IL-10 induced with strain *B. lactis* NCC 2818 (deposited by Nestec SA under CNCM-I3446) was considered as 100%. Finally, the amount of IL-5 induced with IL-4 and anti-CD40 antibody in medium only (i.e. in the absence of probiotics) was set to 100%.

Quantitative Gene Expression Levels by Real-Time PCR:

PBMC ($1.5 \times 10^6$ cells/ml) were cultured in cIMDM with IL-4 (50 ng/ml) and anti-CD40 (1 µg/ml) for 3 days. Thereafter ingredients were added to PBMC and cells were collected after 10 h and 24 h. Total RNA was extracted from stimulated PBMC with SV total RNA isolation system kit (Promega, Wallisellen, Switzerland) including a DNase treatment according to the manufacture's instructions. Total RNA was quantified using the ribogreen RNA quantification kit (Molecular Probes, Basel, Switzerland). Reverse transcription was performed on 1 µg of total RNA by using the Multiscribe Reverse Transcriptase kit (Applied Biosystems, Foster City, Calif., USA). Total RNA was mixed with 50 µM of random hexamers, 0.5 mM of dNTPs, 20 U of RNase inhibitor (Applied Biosystems), 62.5 U of Multiscribe reverse transcriptase, 1× RT buffer, and 5.5 mM of MgCl2 in a final volume of 100 µl. Human IFNγ, IL-10, IL-5, Tbet, GATA3, FoxP3 (Applied Biosystems) were quantified by real time PCR (Applied Biosystems, ABI PRISM 7900HT) using the Taqman gene expression assays. The quantification was normalized with the mean of 3 houses keeping genes: β-actin, GAPDH and HPRT (Applied Biosystems).

Based of the Cycle threshold (Ct) values obtained, a relative and normalized mRNA expression was determined for each gene using the ΔCt. The Ct value for each gene was corrected by the Ct mean of the three house keeping genes. The results were calculated as a relative expression using the formula $2^{-\Delta Ct} \times K$.

OVA Food Allergy Mouse Model:

All studies were approved by a Nestec internal Ethics Committee and the Service Vétérinaire of the Canton of Vaud, Switzerland (Authorization #1970). Six weeks old female conventional BALB/c mice (Harlan Laboratories, France) were sensitized by the oral route (with a gavage needle) at weekly intervals with 20 mg of Ovalbumin (OVA) from Fluka (Buchs, Switzerland)+10 µg/mouse of Cholera toxin (used as adjuvant; List Biologicals, purchase from LuBioscience, Lucerne, Switzerland) during 7 weeks. One week after the last sensitization an oral challenge with 100 mg of OVA was performed. Nutritional intervention with *B. longum* NCC 2705 ($5 \times 10^8$ CFU/ml in drinking water) was done at different phases of the experiment; for primary prevention during sensitisation period, for secondary prevention starting at the end of the sensitization phase, or all along the trial (FIG. 3). Starting 30 minutes after challenge mice were individually observed for 30 min. Clinical symptoms were recorded and quantified as follows (Allergic Score): 0: no symptoms, less than 4 episodes of scratching; 1: 4-10 episodes of scratching around the nose and head, no diarrhoea; 2: more than 10 episodes of scratching or bristled fur and immobility or soft stool; 3: diarrhoea or laboured respiration or cyanosis; 4: diarrhoea in combination with immobility after prodding, bristled fur, laboured respiration or cyanosis; 5: anaphylaxis. Four hours after challenge mice were sacrificed (cervical dislocation), blood and the last centimeter of ileum was taken and frozen in liquid nitrogen.

Serum MMCP-1:

Murine mast cells protease 1 (MMCP-1) was quantified in mouse serum by ELISA, purchased from Moredun Scientific (Penicuik, Scotland) according to the manufacture's instructions. The MMCP-1 concentration was obtained by converting OD values in pg/ml using a polynomial standard curve.

Isolation and Culture of Mesenteric Lymph Node Cells:

Mesenteric lymph nodes (MLN) were homogenized with the plunger of a syringe in a cell strainer (BD Falcon, Milian, Meyrin Switzerland). Cells were centrifuged and washed two times in RPMI (Sigma) complemented with 10% of fetal bovine serum FBS (Bioconcept, Paris, France), 1% L-glutamine (Sigma), 1% Penicillin/Streptomycin (Sigma), 0.1% Gentamycin (Sigma), 0.1% β-mercaptoethanol (Sigma). Cells were cultured in 96 well flat bottom plate (Corning, Milian) in the absence or presence of OVA (1 mg/ml) with $3 \times 10^6$ cells/ml. After 72 h of culture plates were frozen.

Cytokines in Supernatant of MLN Cultures:

Mouse IL-4, IL-5, IL-10, IFN-γ, IL-1β, IL-2, IL-8, TNF-α, IL-12T were measured using the mouse Th1/Th2 9-plex multiplex kit (Meso Scale Discovery, Gaithersburg, Md., USA) according to the manufacture's instructions.

Low Density Array Analyses of Gene Expression in Intestine:

RNA Extraction and Quantification.

Total ribonucleic acids (RNA) from Ileum was extracted according to the manufacture's protocol using the SV Total RNA isolation System kit purchased from Promega (Dübendorf, Switzerland). RNA was quantified with quant-IT Ribogreen Reagent kit provided (Promega Dübendorf, Switzerland) according to the manufacture's protocol.

Reverse Transcription:

Reverse transcription was performed on 1 μg of total RNA by using the Multiscribe Reverse Transcriptase kit from Applied Biosystems (Foster City, Calif., USA). Total RNA was mixed with 50 μM of random hexamers, 0.5 mM of dNTPs, 20 U of RNase inhibitor (Applied Biosystems), 62.5 U of Multiscribe reverse transcriptase, 1× RT buffer, and 5.5 mM of $MgCl_2$ in a final volume of 50 μl. Reverse transcription was run on a T3 thermocycler (Biometra, Göttingen, Germany) with the following cycle program: 10 min at 25° C., 30 min at 48° C., 5 min at 95° C. to finish at 4° C.

Low Density Array (LDA):

LDA were designed online on the Applied Biosytems website (http://www3.appliedbiosystems.com/index.htm). The load, the run and the analysis were performed according to the manufacturer's protocol on a quantitative ABI-Prism 7900HT.

The Quantification was Normalized with the Mean of 3 Houses Keeping Genes:

β-actin, GAPDH and HPRT. Based on the Cycle threshold (Ct) values obtained, a relative and normalized mRNA expression was determined for each gene using the ΔCt. The Ct value for each gene was corrected by the Ct mean of the three house keeping genes. The results were calculated as a relative expression using the formula $2^{-\Delta Ct} \times K$ were K is a $10^6$ factor. Fold increase results expression was normalized to expression levels in the Negative group.

EXAMPLE 1

An example of the composition of an infant formula for use according to the present invention is given below. This composition is given by way of illustration only. The protein source is a conventional mix of whey protein and casein.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| *Bifidobacterium longum* (NCC 2705); see experimental part | $2 \times 10^7$ CFU/g of powder | |

The invention claimed is:

1. A method for reducing symptoms of allergies originating from food allergens comprising the step of administering a complete nutritional composition comprising between $10^4$ and $10^{11}$ colony forming units (CFU) of *Bifidobacterium longum* strain NCC 2705 (CNCM-I2618) per gram of dry composition to a young child below the age of three years who has experienced at least one episode of an allergic reaction from a food allergen selected from the group consisting of milk protein, egg protein, wheat protein, a cereal, a vegetable, a fruit, a nut, and a fish, whereby the symptoms of allergies are reduced.

2. The method of claim 1 wherein the composition further provides the young child with secondary prevention against additional allergic reactions triggered by the food allergens.

3. The method of claim 1 wherein the composition reduces sensitization of the young child to the food allergens.

4. The method of claim 1 wherein the composition comprises between $10^5$ and $10^8$ colony forming units (CFU)

of the *Bifidobacterium longum* strain NCC 2705 (CNCM-I2618) per gram of dry composition.

5. The method of claim 1 wherein the composition comprises at least one prebiotic.

6. The method of claim 1 wherein the composition comprises an apple extract comprising polyphenols and wherein the apple extract helps reduce the symptoms of allergies originating from the food allergens in the young child who has experienced at least one episode of an allergic reaction.

7. The method of claim 1 wherein the composition comprises hydrolyzed proteins.

8. The method of claim 1 wherein the composition reduces the sensitization to the food allergens later in life for the young child.

9. The method of claim 1 wherein the symptoms are selected from the group consisting of gastro-intestinal, cutaneous, respiratory and combination thereof.

10. The method of claim 1 wherein the composition comprises cereal proteins.

11. The method of claim 1 wherein the composition is selected from the group consisting of an infant formula, an infant cereal, liquid composition for children comprising cereals, and a baby food.

12. The method of claim 1 wherein the young child is an infant during the weaning period and/or up to 12 months thereafter.

13. The method of claim 1 wherein the symptoms are accompanied by a release of biochemical mediators.

* * * * *